(12) United States Patent
Bremer

(10) Patent No.: US 6,485,493 B1
(45) Date of Patent: Nov. 26, 2002

(54) SKULL CLOSURE

(76) Inventor: Paul W. Bremer, 4550-1 Saint Augustine Rd., Jacksonville, FL (US) 32207

( * ) Notice: Subject to any disclaimer, the term of this patent is extended or adjusted under 35 U.S.C. 154(b) by 0 days.

(21) Appl. No.: 09/863,767

(22) Filed: May 24, 2001

(51) Int. Cl.[7] ............................................. A61B 17/56
(52) U.S. Cl. ........................... 606/70; 606/72; 606/60; 606/215
(58) Field of Search ................. 606/72, 215, 213, 606/60, 70, 73, 77, 76, 75

(56) References Cited

U.S. PATENT DOCUMENTS 5,707,373 A * 1/1998 Servain et al.
6,022,351 A * 2/2000 Bremer et al.
6,258,091 B1 * 7/2001 Sevrain et al.
6,328,743 B2 * 12/2001 Lerch

* cited by examiner

Primary Examiner—Pedro Philogene
(74) Attorney, Agent, or Firm—Nixon & Vanderhye

(57) ABSTRACT

A fastener system for use in reattaching a skull flap in an opening formed in a patient's skull during brain surgery is simple, quick and easy to use, and cost effective. The system includes a fastener element and a substantially disc shaped lock element. The fastener element has a shank with a plurality of ratchet teeth, and a plurality ridges extending upwardly from the shank a distance greater than the height of the ratchet teeth, and substantially perpendicular to the ratchet teeth. The ridges engage at least one of the skull and skull flap and either bend or collapse, or cut locking grooves into the skull or skull flap, to provide a force holding the shank in engagement with the skull and skull flap. The lock element may have force concentrating projections extending outwardly toward the fastener head, and the head may have a plurality of resilient[ outrigger leaves.

35 Claims, 2 Drawing Sheets

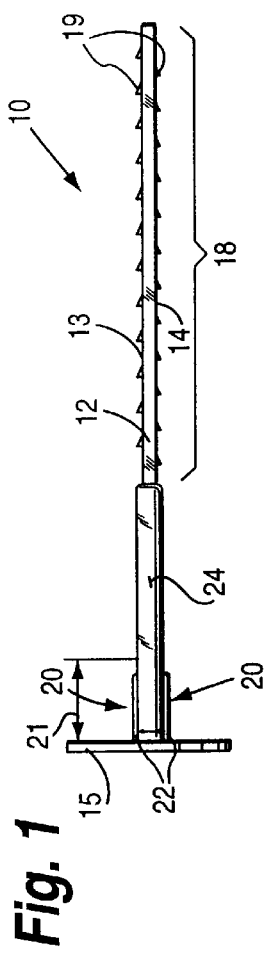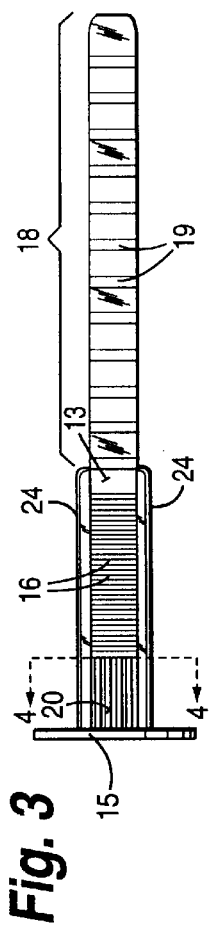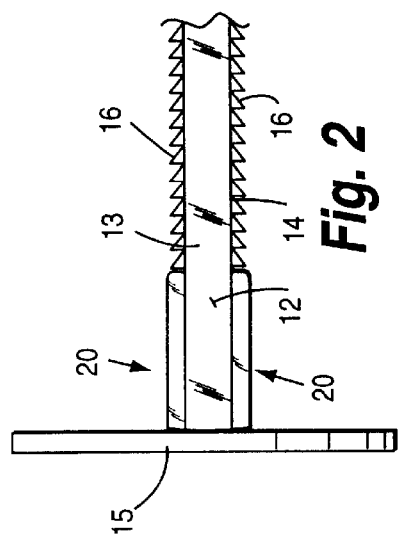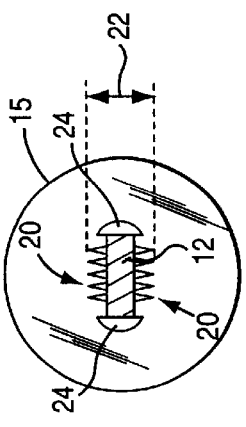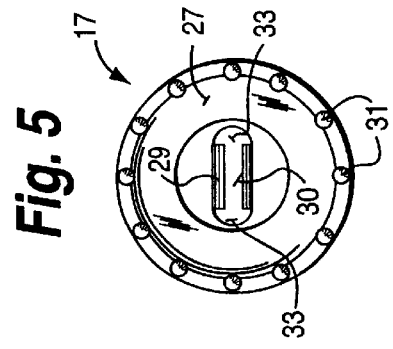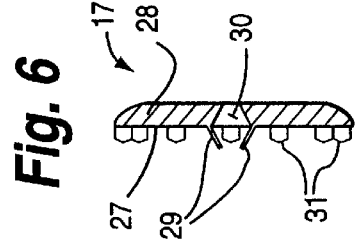

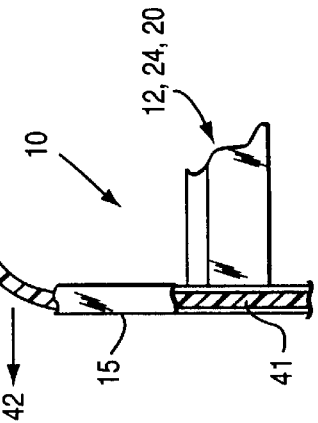
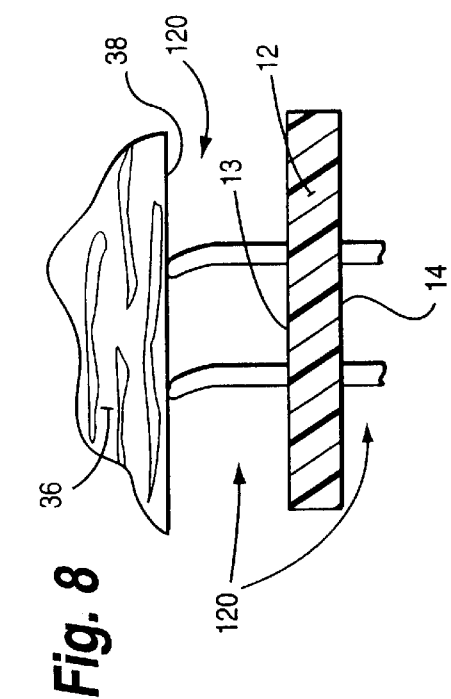
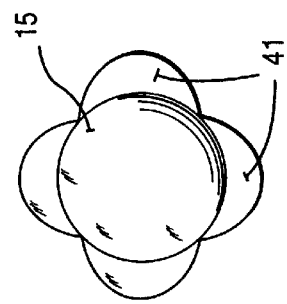
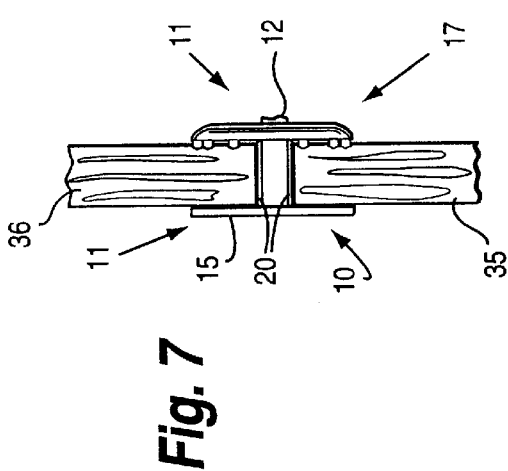
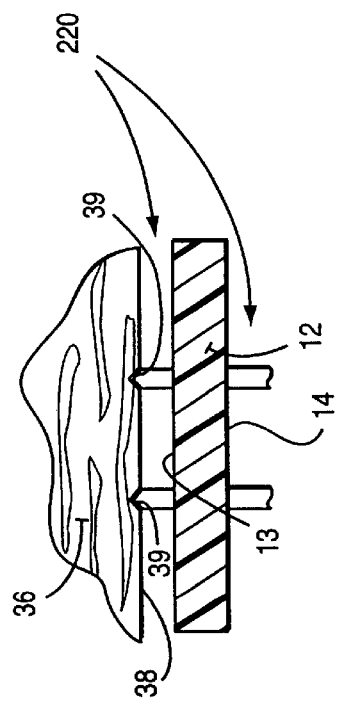

SKULL CLOSURE

BACKGROUND AND SUMMARY OF THE INVENTION

U.S. Pat. No. 6,022,351 (the disclosure of which is hereby incorporated by reference herein) has provided a significant advance in the art of bone fastening systems during surgical or related medical procedures, in reattaching a skull flap. The invention provides an improvement over the system and method of the U.S. Pat. No. 6,022,351 patent, particularly in providing an enhanced force holding the shank in engagement with the skull and skull flap, and in addition other features are provided that facilitate holding the locking element in place, and facilitate maintaining the fastener and locking elements clamped together in a position holding the skull flap in place. These advantageous results are provided according to the present invention by utilizing a plurality of ridges extending from the fastener head generally perpendicular to the ratchet teeth, and extending upwardly from the fastener shank substantially flat surfaces; by providing a plurality of force concentrating projections on the locking element disc extending axially with respect to the disc; and by providing side walls on the shank having approximately the height of the ratchet teeth, and engaged in side portions of the opening in the locking element.

According to one aspect of the present invention there is provided a fastening system comprising: A fastener element of bio-compatible radiolucent plastic material comprising a substantially disc shaped head and a shank. The shank having substantially flat first and second substantially parallel surfaces, the surfaces having ratchet teeth thereon. A substantially disc shaped lock element of bio-compatible radiolucent rigid plastic material having a through extending opening and locking teeth defining at least part of the opening, the locking teeth cooperating with the ratchet teeth to allow the shank to pass through the opening so that the head and lock element can be forced toward each other, but not allowing movement away from each other. And, a plurality of ridges extending upwardly from at least one of the first and second substantially parallel surfaces adjacent the head, the ridges extending substantially perpendicular to the ratchet teeth.

The ridges may be of two different types, both of which provide a force holding the shank in engagement with the skull and skull flap. The first type of ridges may be of relatively soft plastic, and constructed so that in use the ridges bend or collapse and provide a wedging action against a bone surface engaged thereby. Another alternative is to provide the ridges out of a hard plastic or metal and construct them so that in use the ridges cut locking grooves in a bone surface engaged thereby. In either case the stability of the fastening system is enhanced, as is its ability to hold the skull flap properly in place.

The ridges may be about 3–7 mm long, and typically substantially abut the fastener head. Desirably the ridges upstand from both the first and second surfaces of the shank, and the distance from the tip of a ridge extending upwardly from the first surface to the tip of a ridge extending upwardly from the second surface is between about 2–5 mm, most desirably about 3–3.5 mm. Typically between two and six ridges are provided (extending upwardly from each of the first and second surfaces). The shank may have a thickness of about 1–1.5 mm.

Also the shank may have first and second exterior side walls extending over a portion of the length thereof including past the ridges, and at least some of the ratchet teeth. The locking element opening has first and second side portions for receiving the side walls. For example the side walls extend upwardly past the first and second shank surfaces a distance approximately equal to the heights of the ratchet teeth, and less than the height of the ridges. For example in one embodiment the shank has a basic thickness of about 1 mm, and at the side walls a thickness of about 2 mm, and at the ridges a thickness of about 3 mm.

The lock element typically has first and second faces and a plurality of force concentrating projections extending outwardly from the first face, toward the fastener head in use. The locking teeth also typically extend outwardly from the first face. The fastener head may have a plurality of resilient outrigger leaves, which may be deformed during the clamping operation, to provide a force enhancing the clamping action.

According to another aspect of the present invention there is provided a method of reattaching a skull flap, removed during brain surgery and leaving an opening in a patient's skull, the flap having an area less than the area of the opening but substantially the same shape, and using a fastening system, comprising a fastener element made of bio-compatible radiolucent rigid plastic having a shank with ratchet teeth and a substantially disc shaped lock element with an opening defined at least in part by at least one locking tooth, and a plurality of ridges upstanding from the shank and extending substantially perpendicular to the ratchet teeth. The method comprises: (a) Placing a plurality of fastener heads, with shanks facing outwardly, in the skull opening. (b) Placing the skull flap in the skull opening so that a gap is provided between the outer periphery of the skill flap and the periphery of the skull opening, and the fastener shanks extend through the gap and the ridges engage at least one of the skull and the skull flap and provide a force holding the shank in operative engagement with the skull and skull flap. (c) Placing the lock elements over the shanks. (d) For each fastener forcing the lock toward the head so that the ratchet teeth and at least one locking tooth move with respect to each other, until the head and lock element are locked together holding the skull flap in a position closing the skull opening. And, (e) removing substantially all shank portions extending outwardly from the lock elements.

In the method (b) may be practiced so that the ridges engage both the skull and the skull flap. When the ridges are of soft plastic and constructed so that they bend or collapse, then (b) is practiced so that the ridges bend or collapse so as to provide a wedging action holding the shank between the skull and skull flap. When the ridges are of hard plastic or metal and are constructed so that they can cut locking grooves into the bone, then (b) is practiced so as to cut locking grooves in the skull and skull flap so as to lock the shank in place therebetween. When a locking element has a plurality of substantially axially extending force concentrating projections, then (d) is practiced so as to cause the force concentrating projection to engage at least one of the skull and skull flap to enhance securement of the locking element to the skull and/or skull flap. Preferably (d) is practiced so that the force concentrating elements operatively engage both the skull and skull flap.

According to another aspect of the present invention there is provided a fastener system comprising: A fastener element of bio-compatible radiolucent rigid plastic material comprising a substantially disc shaped head and a shank. The shank having a plurality of ratchet teeth thereon, and a thickness of about 7 mm or less. A substantially disc shaped lock of bio-compatible radiolucent plastic material having a through extending opening into at least one locking tooth defining at least part of the opening, the at least one locking tooth cooperating with the ratchet teeth to allow the shank to pass through the opening so that the head and lock can be forced toward each other, but not allowing movement away from each other. And, wherein the lock element has first and second faces, and a plurality of force concentrating projections extending outwardly from the first face, toward the head in use. The details of the first concentrating projections may be as set forth above.

According to another aspect of the present invention there is provided a fastener system comprising: A fastener element of bio-compatible radiolucent rigid plastic material comprising a substantially disc shaped head and a shank. The shank having a plurality of ratchet teeth thereon, and a thickness of about 7 mm or less. A substantially disc shaped lock of bio-compatible radiolucent plastic material having a through extending opening into at least one locking tooth defining at least part of the opening, the at least one locking tooth cooperating with the ratchet teeth to allow the shank to pass through the opening so that the head and lock can be forced toward each other, but not allowing movement away from each other. And, wherein the head has a plurality of resilient outrigger leaves.

For example in the fastening system set forth above, the shank has a plurality of ridges substantially abutting the head and extending substantially perpendicular to the ratchet teeth a distance of about 3–7 mm from the head; and typically the shank itself has a thickness of about 1–1.5 mm, and the shank including the ridges has a thickness of about 2–5 mm.

According to yet another aspect of the present invention there is provided a fastener system comprising: A fastener element of bio-compatible radiolucent rigid plastic material comprising a substantially disc shaped head and a shank. The shank having a plurality of ratchet teeth thereon, and a thickness of about 7 mm or less. A substantially disc shaped lock of bio-compatible radiolucent plastic material having a through extending opening into at least one locking tooth defining at least part of the opening, the at least one locking tooth cooperating with the ratchet teeth to allow the shank to pass through the opening so that the head and lock can be forced toward each other, but not allowing movement away from each other. And, wherein the shank has first and second exterior side walls extending over a portion of the length thereof including past at least some of the ratchet teeth; and wherein the locking element opening has first and second side portions for receiving the side walls. In this embodiment typically the side walls extend past the first and second shank surfaces a distance approximately equal to the height of the ratchet teeth, e.g. the total thickness of the shank at the side walls is about 2 mm.

It is the primary object of the present invention to provide an enhanced fastening system, and method of utilization thereof, particularly suitable for reattaching a skull flap in a skull after brain surgery. However the invention has other uses in association with other bones and suitable medical procedures. This and other objects of the invention will become clear from an inspection of the detailed description of the invention and from the appended claims.

BRIEF DESCRIPTION OF THE DRAWINGS

FIG. 1 is a greatly enlarged side view of one embodiment of an exemplary fastener element according to the present invention;

FIG. 2 is a detail view of the fastener element of FIG. 1 with the side walls removed for clarity of illustration of the ratchet teeth and perpendicular ridges;

FIG. 3 is a top plan view of the fastener element of FIG. 1;

FIG. 4 is a cross-sectional view of the fastener element of FIG. 3 taken along lines 4—4 thereof;

FIG. 5 is an end view of an exemplary locking element utilizable with the fastener of FIG. 1, according to the present invention;

FIG. 6 is a longitudinal cross-sectional view of the locking element of FIG. 5;

FIG. 7 is a side schematic view, with the skull and skull flap shown in cross-section and the fastening system in elevation, of the utilization of the fastener element of FIG. 1 and the locking element of FIG. 5 to hold the skull flap in place with respect to the surrounding skull;

FIG. 8 is a detail schematic view showing the action of one embodiment of ridges of the fastener element in providing a wedging action when utilized in the manner illustrated in FIG. 7;

FIG. 9 is a view like that of FIG. 8 only showing different ridges which cut grooves in the surrounding bone when utilized in the manner illustrated in FIG. 7;

FIG. 10 is a top plan view of the head of a second embodiment of fastener element according to the present invention; and FIG. 11 is a side schematic view of a portion of the head of FIG. 10 particularly showing curvature of the resilient outrigger leaves thereof.

DETAILED DESCRIPTION OF THE DRAWINGS

For the exemplary embodiment of the fastener element 10 of the fastening system according to the present invention (shown schematically at 11 in use, in FIG. 7), where features are the same as in U.S. at. No. 6,022,351 they are not explained in detail herein, but rather reference is made to the U.S. Pat. No. 6,022,351 patent (which has been incorporated by reference herein).

The fastening element 10 of FIGS. 1 through 4 includes a shank portion 12 which typically has a thickness of about 1–2 mm, preferably about 1 mm, and substantially flat first and second surfaces 13, 14. The shank 12 is integral with a substantially disc-shaped head 15, and ratchet teeth 16 extend upwardly from one, and preferably both, surfaces 13, 14 as seen most clearly in FIGS. 1 and 2. Closer to the head 15, where the ratchet teeth 16 must operatively engage and provide a clamping action with the locking element shown generally at 17 in FIGS. 5 through 7, the ratchet teeth 16 are spaced immediately adjacent each other, whereas in the portion of the shank 12 indicated by reference numeral 18 in FIGS. 1 and 3 the ratchet teeth may be spaced much more widely from each other, the widely spaced ratchet teeth being shown generally by reference numeral 19. For the section 18 of the shank 12 the ratchet teeth 19 merely provide a mechanism to prevent the locking element 17 from falling off of the fastener element 10 during use or handling but do not provide a clamping action, as is provided by the teeth 16 on the portion of the shank 12 closer to the head 15.

According to the present invention adjacent the head 15 a plurality of ridges 20 are provided upwardly extending from at least one of the surfaces 13, 14, and preferably extending upwardly from both of the surfaces 13, 14. The ridges 20 may abut the head 15, as illustrated in FIGS. 1 through 3, and extend substantially perpendicular to the ratchet teeth 16, that is extend in the dimension of elongation of the shank 12. The ridges 20 are preferably substantially parallel to each other, and between two and six ridges are typically provided extending upwardly from each of the surfaces of 13, 14. The ridges 20 preferably extend a distance (have a length) 21 from the head 15 which is between about 3–7 mm, e.g. about 5 mm. The distance may depend upon the thickness of the skull with which the fastener system 11 is utilized. The dimension 22 from the top of one ridge 20 extending from the surface 13 to the top of an aligned ridge 20 extending from the surface 14 is typically about 2–5 mm, preferably about 3 mm. The distance 22 will depend upon the particular materials of which the ridges 20 are made, and the spacing between the skull flap and skull during a brain operation.

In the embodiment illustrated in FIGS. 1 through 4 the fastener element 10 also preferably has exterior side walls 24 (cut away in FIG. 2) each of which has a height that is greater than the thickness of the shank 12; for example if the thickness of the shank 12 is about 1 mm, the height of each of the walls 24 is about 2 mm. The side walls 24 typically have a height that is less than the height (distance 22) of the ridges 20; for example if the side walls 24 have a height of about 2 mm the distance 22 is about 3 mm.

The substantially disc-shaped locking element 17 of FIGS. 5 and 6 has a slightly different construction than the corresponding locking element in U.S. Pat. No. 6,022,351. The substantially disc-shaped locking element 17 has a first surface 27 and a second surface 28. The one or more locking teeth 29 extend outwardly from the surface 27, adjacent the through-extending opening 30. Also extending outwardly from the surface 27, preferably around the periphery of the disc forming the locking element 17 (as seen in FIGS. 5 and 6), are a plurality of force concentrating projections 31, each of which typically has a sharp tip as illustrated in FIGS. 5 and 6. The projections 31 facilitate clamping action by providing excellent engagement of either or both of (depending upon where the force concentrating projections 31 are located) the skull and the skull flap of a human or animal with which the fastening system 11 is utilized.

The opening 30 also preferably has side portions thereof exteriorly of the locking teeth 29 that are dimensioned to receive the side walls 24 therein, and to provide rotational stability to the fastening system 11 so that the elements 10, 17 do not have a tendency to rotate with respect to each other.

FIG. 7 schematically illustrates one of the fastening systems 11 in use in holding a skull flap 35 to the surrounding bone of the skull 36. Note that the ridges 20 engage the surfaces of the skull flap 35 and the skull 36 (preferably engaging both of them, but engaging at least one) to provide a force holding the shank 12 in operative engagement with the skull and the skull flap 36, 35. In the position illustrated in FIG. 7, as for the system shown in U.S. Pat. No. 6,022,351, the shank 12 has been broken off and the locking teeth 29 of the locking element 17 engage ratchet teeth 16 and tightly hold the head 15 in engagement with the substantially flat surfaces of both the skull flap 35 and skull 36, while the force concentrating elements 31 of the locking element 17 provide secure engagement with the opposite substantially flat faces of the skull flap 35 and skull 36. A plurality of such fastening systems 11 are utilized, as illustrated in FIGS. 6 and 7 of the U.S. Pat. No. 6,022,351 patent, according to the preferred embodiment of the invention.

FIGS. 8 and 9 schematically show in detail from an end view two alternative types of engagement that may be provided between the teeth 20 and the skull 36 and/or skull flap 35, in the practice of the method according to the invention utilizing the fastener system 11. In the FIG. 8 embodiment relatively soft ridges are utilized, which are shown by reference numeral 120, whereas in FIG. 9 relatively hard ridges are illustrated, shown generally by reference numeral 220.

In the FIG. 8 embodiment, which is not to scale, but merely for schematic illustrative purposes, the ridges 120 (two of which are shown, but typically between two and six are provided associated with each of the surfaces 13, 14 of the shank 12) engage the substantially flat surface 38 of the skull 36 which has been cut with a bone saw during the brain operation. The ridges 120 are much longer than they are thick, and are of relatively soft plastic so that they have a tendency to bend or collapse, as illustrated in FIG. 8, when inserted between the skull 36 and skull flap 35. This bending or collapsing action illustrated in FIG. 8 provides a wedging action which enhances the holding action of the shank 12 with respect to the skull 36 and skull flap 35 so that a combination of this wedging action and the clamping provided by the locking element 17 engaging the ratchet teeth 16 and the head 15 engaging the skull 36 and skull flap 35, provides a very secure holding action, to securely hold the skull flap 35 in place.

In the embodiment illustrated in FIG. 9, the ridges 220 have a squatter configuration and are of hard material, such as hard plastic or metal, so that instead of bending or collapsing as illustrated in FIG. 8, when the fastener element 10 is inserted into place between the skull flap 35 and the skull 36, the ridges 220 actually cut grooves 39 in the bone of the skull 36 (and/or skull flap 35), again enhancing the force holding the shank 12 in engagement with the skull 36 and skull flap 35.

FIGS. 10 and 11 show another embodiment that the head 15 of the fastener element 10 may have. In this embodiment the head 15 has a plurality of outrigger leaves 41 of a resilient construction and/or material, and are preferably curved toward the face of the head 15 from which the shank 12 extends (as seen in FIG. 11). With this construction, as the fastener system 11 is clamped into place as illustrated in FIG. 7, the outrigger leaves 41 are flexed, as indicated by arrow 42 in FIG. 11, so that when the fastener system 11 is clamped in place the resilient force provided by the outrigger leaves 41 tending to return to the curved position illustrated in FIG. 11 enhances the clamping action provided for the fastener 11.

In the practice of the method according to the present invention, a plurality of fastener heads 15 with shanks 12 facing outwardly are placed in the skull opening, inside the surface 38 of the skull 36. Then the skull flap 35 is placed in the skull opening so that a gap is provided between the outer periphery of the skull flap 35 and the periphery 38 of the skull opening and the fastener shanks 12 extend in the gap as seen in FIGS. 7 through 9, and the ridges 20,120, 220 engage at least one of the skull 36 and the skull flap 35 and provide a force holding the shank in operative engagement therewith [either a wedging action by deformation of the ridges 120 as illustrated in FIG. 8, or a cutting action as shown for the ridges 220 in FIG. 9]. Then the lock elements 17 are placed over the shanks 12, each lock 17 is forced toward the head 15 so that the ratchet teeth 16 and the locking teeth 29 move with respect to each other until the head 15 and lock element 17 are locked together holding the skull flap 35 in a position closing the skull opening (as seen in FIG. 7). Once element 17 moves past a tooth 16 it cannot move backwardly over it again. Then one removes substantially all of the shank 12 portions extending outwardly from the lock element 17, such as by clipping or in other manners described in U.S. Pat. No. 6,022,351.

Each of the ranges described herein also specifically includes all smaller ranges within a broad range. For example the dimension of 2–5 mm for the combined height of the ridges 20 and shank 12 (the distance 22) specifically includes 2.5–3.1 mm, 3.1–4.2 mm, and all other narrower ranges within the about 2–5 mm range.

It will thus be seen that according to the present invention an improved fastening system and method of reattaching a skull flap are provided. While the invention has been herein shown and described in what is presently conceived to be the most practical and preferred embodiment thereof it will be apparent to those of ordinary skill in the art that many modifications may be made thereof within the scope of the invention, which scope is to be accorded the broadest interpretation of the appended claims so as to encompass all equivalent structures and methods.

What is claimed is:

1. A fastening system comprising:
   a fastener element of bio-compatible radiolucent plastic material comprising a substantially disc shaped head and a shank;
   said shank having substantially flat first and second substantially parallel surfaces, said surfaces having ratchet teeth thereon;
   a substantially disc shaped lock element of bio-compatible radiolucent rigid plastic material having a through extending opening and locking teeth defining at least part of said opening, said locking teeth cooperating with said ratchet teeth to allow said shank to pass through said opening so that said head and lock element can be forced toward each other, but not allowing movement away from each other; and
   a plurality of ridges extending upwardly from at least one of said first and second substantially parallel surfaces adjacent said head, said ridges extending substantially perpendicular to said ratchet teeth.

2. A system as recited in claim 1 wherein said ridges upstand from both said first and second surfaces, and wherein said ridges are of relatively soft plastic and constructed so that in use said ridges bend or collapse and provide a wedging action against a bone surface engage thereby.

3. A system as recited in claim 1 wherein said ridges are of hard plastic or metal and constructed so that in use said ridges cut locking grooves in a bone surface engaged thereby.

4. A system as recited in claim 1 wherein said ridges are about 3–7 mm long.

5. A system as recited in claim 4 wherein said ridges substantially abut said head.

6. A system as recited in claim 5 wherein said ridges upstand from both said first and second surfaces, and wherein the distance from the tip of a ridge extending upwardly from said first surface to the tip of a ridge extending upwardly from said second surface is between about 2–5 mm.

7. A system as recited in claim 1 wherein said ridges upstand from both said first and second surfaces, and wherein the distance from the tip of a ridge extending upwardly from said first surface to the tip of a ridge extending upwardly from said second surface is between about 2–5 mm.

8. A system as recited in claim 1 wherein said lock element has first and second faces, and a plurality of force concentrating projections extending outwardly from said first face, toward said head in use.

9. A system as recited in claim 8 wherein said locking teeth extend outwardly from said first face.

10. A system as recited in claim 9 wherein said head has a plurality of resilient outrigger leaves.

11. A system as recited in claim 1 wherein said head has a plurality of resilient outrigger leaves.

12. A system as recited in claim 1 wherein said shank itself has a thickness of about 1–1.5 mm, and at said ridges a thickness of about 2–5 mm.

13. A system as recited in claim 2 wherein said shank itself has a thickness of about 1–1.5 mm, and at said ridges a thickness of about 2–5 mm.

14. A system as recited in claim 3 wherein said shank itself has a thickness of about 1–1.5 mm, and at said ridges a thickness of about 2–5 mm.

15. A system as recited in claim 12 wherein said ridges are about 3–7 mm long.

16. A system as recited in claim 1 wherein said shank has first and second exterior side walls extending over a portion of the length thereof including past said ridges and at least some of said ratchet teeth; and wherein said locking element opening has first and second side portions for receiving said side walls.

17. A system as recited in claim 16 wherein said side walls extend upwardly past said first and second shank surfaces a distance approximately equal to the heights of said ratchet teeth, and less than the height of said ridges.

18. A system as recited in claim 17 wherein said shank has a basic thickness of about 1 mm, and at said side walls a thickness of about 2 mm and at said ridges a thickness of about 3 mm.

19. A system according to claim 1 wherein said shank includes first and second exterior side walls having a height in a direction generally perpendicular to the substantially flat first and second parallel surfaces of said shank greater than a thickness of said shank between said first and second parallel surfaces.

20. A method of reattaching a skull flap, removed during brain surgery and leaving an opening in a patient's skull, the flap having an area less than the area of the opening but substantially the same shape, and using a fastening system, comprising a fastener element made of bio-compatible radiolucent rigid plastic having a shank with ratchet teeth and a substantially disc shaped lock element with an opening defined at least in part by at least one locking tooth, and a plurality of ridges upstanding from the shank and extending substantially perpendicular to the ratchet teeth; said method comprising:
   (a) placing a plurality of fastener heads, with shanks facing outwardly, in the skull opening;
   (b) placing the skull flap in the skull opening so that a gap is provided between the outer periphery of the skull flap and the periphery of the skull opening, and the fastener shanks extend through the gap and the ridges engage at least one of the skull and the skull flap and provide a force holding the shank in operative engagement with the skull and skull flap;
   (c) placing the lock elements over the shanks;
   (d) for each fastener forcing the lock toward the head so that the ratchet teeth and at least one locking tooth move with respect to each other, until the head and lock element are locked together holding the skull flap in a position closing the skull opening; and
   (e) removing substantially all shank portions extending outwardly from the lock elements.

21. A method as recited in claim 20 wherein (b) is practiced so that ridges engage both the skull and skull flap.

22. A method as recited in claim 21 wherein the ridges are of soft plastic and constructed so that they bend or collapse; and wherein (b) is practiced so that the ridges bend or collapse so as to provide a wedging action holding the shank between the skull and skull flap.

23. A method as recited in claim 21 wherein the ridges are of hard plastic or metal and are constructed so that they can cut locking grooves in bone; and wherein (b) is practiced so as to cut locking grooves in the skull and skull flap so as to lock the shank in place therebetween.

24. A method as recited in claim 20 wherein the ridges are of hard plastic or metal and are constructed so that they can cut locking grooves in bone; and wherein (b) is practiced so as to cut locking grooves in the skull or skull flap so as to lock the shank in place therebetween.

25. A method as recited in claim 20 wherein the ridges are of soft plastic and constructed so that they bend or collapse; and wherein (b) is practiced so that the ridges bend or collapse so as to provide a wedging action holding the shank between the skull and skull flap.

26. A method as recited in claim 20 wherein the locking element has a plurality of substantially axially extending force concentrating projections; and wherein (d) is practiced so as to cause the force concentrating projection to engage at least one of the skull and skull flap to enhance securement of the locking element to the skull or skull flap.

27. A method as recited in claim 26 wherein (d) is practiced so that the force concentrating elements operatively engage both the skull and skull flap.

28. A fastener system comprising:

a fastener element of bio-compatible radiolucent rigid plastic material comprising a substantially disc shaped head and a shank;

said shank having a plurality of ratchet teeth thereon, and a thickness of about 7 mm or less;

a substantially disc shaped lock of bio-compatible radiolucent plastic material having a through extending opening and at least one locking tooth defining at least part of said opening, said at least one locking tooth cooperating with said ratchet teeth to allow said shank to pass through said opening so that said head and lock can be forced toward each other, but not allowing movement away from each other; and wherein said lock element has first and second faces, and a plurality of force concentrating projections extending outwardly from said first face, toward said head in use and said head has a plurality of flexible, resilient outrigger leaves.

29. A system as recited in claim 28 wherein said locking tooth extends outwardly from said first face.

30. A fastener system comprising:

a fastener element of bio-compatible radiolucent rigid plastic material comprising a substantially disc shaped head and a shank;

said shank having a plurality of ratchet teeth thereon, and a thickness of about 7 mm or less;

a substantially disc shaped lock of bio-compatible radiolucent plastic material having a through extending opening and at least one locking tooth defining at least part of said opening, said at least one locking tooth cooperating with said ratchet teeth to allow said shank to pass through said opening so that said head and lock can be forced toward each other, but not allowing movement away from each other; and wherein said head has a plurality of resilient outrigger leaves, said shank having a plurality of ridges substantially abutting said head and extending substantially perpendicular to said ratchet teeth a distance of about 3–7 mm from said head.

31. A system as recited in claim 30 wherein said shank itself has a thickness of about 1–1.5 mm, and at said ridges a thickness of about 2–5 mm.

32. A fastener system comprising:

a fastener element of bio-compatible radiolucent rigid plastic material comprising a substantially disc shaped head and a shank;

said shank having a plurality of ratchet teeth thereon, and a thickness of about 7 mm or less;

a substantially disc shaped lock of bio-compatible radiolucent plastic material having a through extending opening and at least one locking tooth defining at least part of said opening, said at least one locking tooth cooperating with said ratchet teeth to allow said shank to pass through said opening so that said head and lock can be forced toward each other, but not allowing movement away from each other; and wherein said lock element has first and second faces, and a plurality of force concentrating projections extending outwardly from said first face, toward said head in use, said shank having a plurality of ridges substantially abutting said head and extending substantially perpendicular to said ratchet teeth a distance of about 3–7 mm from said head.

33. A system as recited in claim 32 wherein said shank itself has a thickness of about 1–1.5 mm, and at said ridges a thickness of about 2–5 mm.

34. A fastener system comprising:

a fastener element of bio-compatible radiolucent rigid plastic material comprising a substantially disc shaped head and an elongated shank extending from said head;

said shank having a plurality of ratchet teeth thereon, and a thickness of about 7 mm or less;

a substantially disc shaped lock of bio-compatible radiolucent plastic material having a through extending opening and at least one locking tooth defining at least part of said opening, said at least one locking tooth cooperating with said ratchet teeth to allow said shank to pass through said opening so that said head and lock can be forced toward each other, but not allowing movement away from each other; and wherein said shank has first and second exterior side walls extending over a portion of the length thereof including past at least some of said ratchet teeth; each of said first and second exterior side walls having a height in a direction generally perpendicular to said shank greater than the thickness of said shank; and wherein said locking element opening has first and second side portions for receiving said side walls.

35. A system as recited in claim 34 wherein said side walls extend past said first and second shank surfaces in said generally perpendicular direction a distance approximately equal to the heights of said ratchet teeth.

* * * * *